(12) United States Patent
Varanasi et al.

(10) Patent No.: US 7,845,213 B2
(45) Date of Patent: Dec. 7, 2010

(54) VOLATILE LIQUIDS HAVING PREDETERMINED EVAPORATION PROFILES

(75) Inventors: Padma Prabodh Varanasi, Racine, WI (US); Joel E. Adair, Racine, WI (US); Michael C. Liptrot, Milwaukee, WI (US); Qing Song, Madison, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 12/771,765

(22) Filed: Apr. 30, 2010

(65) Prior Publication Data

US 2010/0206960 A1 Aug. 19, 2010

Related U.S. Application Data

(63) Continuation of application No. 10/608,357, filed on Jun. 27, 2003, now Pat. No. 7,744,833.

(51) Int. Cl.
| | |
|---|---|
| *A61L 9/00* | (2006.01) |
| *A62B 7/08* | (2006.01) |
| *B01D 47/06* | (2006.01) |
| *B01D 47/16* | (2006.01) |
| *F24F 6/08* | (2006.01) |
| *A01G 13/06* | (2006.01) |
| *B05B 1/08* | (2006.01) |
| *B05B 17/04* | (2006.01) |
| *A61M 11/06* | (2006.01) |
| *G01N 13/00* | (2006.01) |

(52) U.S. Cl. ............... 73/64.52; 422/1; 422/5; 422/120; 422/123; 422/124; 422/125; 422/305; 422/900; 261/78.1; 261/94; 261/97; 261/99; 392/394; 392/395; 392/386; 239/102.1; 239/102.2; 239/4; 239/338; 34/DIG. 1

(58) Field of Classification Search ............ 422/1, 422/5, 120, 123–125, 305–306, 900; 261/78.1, 261/94, 97, 99; 392/394–395, 386; 239/102.1, 239/102.2, 4, 338; 73/64.52; 34/DIG. 1

See application file for complete search history.

(56) References Cited

U.S. PATENT DOCUMENTS 1,129,897 A 3/1915 Owen, Jr.

(Continued)

FOREIGN PATENT DOCUMENTS

AU 664685 11/1995

(Continued)

OTHER PUBLICATIONS

International Search Report and Written Opinion, Aug. 16, 2004, Appl. No. PCT/US04/008436.

(Continued)

*Primary Examiner*—Jill Warden
*Assistant Examiner*—Monzer R Chorbaji

(57) ABSTRACT

Dispensers and refills for volatile liquids, such as fragrances, are disclosed. Dispensers and refills in combination with dispensers according to the present invention may comprise a volatile liquid and a housing. In certain embodiments, the volatile liquid of the present invention has a predetermined evaporation rate, measured and calculated by the method described herein. In other embodiments, the volatile liquid exhibits a predefined relative evaporation rate. In addition to the housing, the present invention includes optional components, such as a motorized fan and/or a wick, to facilitate release of the volatile liquid into the atmosphere.

16 Claims, 2 Drawing Sheets

U.S. PATENT DOCUMENTS

| | | |
|---|---|---|
| 1,911,871 A | 5/1933 | Anderson |
| 2,435,811 A | 2/1948 | Waters |
| 2,472,992 A | 6/1949 | Szckcly |
| 2,557,501 A | 6/1951 | Fusay et al. |
| 2,754,554 A | 7/1956 | Mills |
| 2,764,789 A | 10/1956 | Zelenka |
| 2,828,953 A | 4/1958 | Hartmann |
| 2,867,866 A | 1/1959 | Steele |
| 2,897,671 A | 8/1959 | Phelan et al. |
| 3,080,624 A | 3/1963 | Weber, III |
| 3,102,101 A | 8/1963 | Hawley et al. |
| 3,550,853 A | 12/1970 | Gray |
| 3,587,968 A | 6/1971 | Balland et al. |
| 3,633,881 A | 1/1972 | Yurdin |
| 3,748,464 A | 7/1973 | Andeweg |
| 3,749,904 A | 7/1973 | Graff |
| 3,761,702 A | 9/1973 | Andeweg |
| 3,790,081 A | 2/1974 | Thornton et al. |
| 3,804,592 A | 4/1974 | Garbe |
| 3,890,085 A | 6/1975 | Andeweg |
| 3,903,022 A | 9/1975 | Ohara et al. |
| 3,923,458 A | 12/1975 | Moran |
| 3,948,445 A | 4/1976 | Andeweg |
| 3,979,179 A | 9/1976 | Teng |
| 3,990,848 A | 11/1976 | Corris |
| 3,993,444 A | 11/1976 | Brown |
| 4,035,451 A | 7/1977 | Tringali |
| 4,166,087 A | 8/1979 | Cline et al. |
| 4,173,604 A | 11/1979 | Dimacopoulos |
| 4,276,236 A | 6/1981 | Sullivan et al. |
| 4,294,778 A | 10/1981 | DeLuca |
| 4,323,193 A | 4/1982 | Compton et al. |
| 4,346,059 A | 8/1982 | Spector |
| 4,383,951 A | 5/1983 | Palson |
| 4,387,849 A | 6/1983 | Van Loveren et al. |
| 4,419,326 A | 12/1983 | Santini |
| 4,432,938 A | 2/1984 | Meetze, Jr. |
| 4,445,641 A | 5/1984 | Baker et al. |
| 4,493,011 A | 1/1985 | Spector |
| 4,605,165 A | 8/1986 | Van Loveren et al. |
| 4,614,299 A | 9/1986 | Van Loveren et al. |
| 4,621,768 A | 11/1986 | Lhoste et al. |
| 4,660,764 A | 4/1987 | Joyaux et al. |
| 4,666,638 A | 5/1987 | Baker et al. |
| 4,695,435 A | 9/1987 | Spector |
| 4,707,338 A | 11/1987 | Spector |
| 4,739,928 A | 4/1988 | O'Neil |
| 4,743,406 A | 5/1988 | Steiner et al. |
| 4,857,240 A | 8/1989 | Kearnes et al. |
| 4,866,580 A | 9/1989 | Blackerby |
| 4,913,350 A | 4/1990 | Purzycki |
| 4,928,881 A | 5/1990 | Barlics et al. |
| 4,931,224 A | 6/1990 | Holzner, Sr. |
| 4,968,487 A | 11/1990 | Yamamoto et al. |
| 5,081,104 A | 1/1992 | Orson, Sr. |
| RE33,864 E | 3/1992 | Steiner et al. |
| 5,094,025 A | 3/1992 | Daniels |
| 5,095,647 A | 3/1992 | Zobele et al. |
| 5,114,625 A | 5/1992 | Gibson |
| 5,126,078 A | 6/1992 | Steiner et al. |
| 5,133,042 A | 7/1992 | Pelonis |
| 5,217,696 A | 6/1993 | Wolverton et al. |
| 5,222,186 A | 6/1993 | Schimanski et al. |
| 5,223,182 A | 6/1993 | Steiner et al. |
| 5,324,490 A | 6/1994 | Van Vlahakis et al. |
| 5,342,584 A | 8/1994 | Fritz et al. |
| 5,370,829 A | 12/1994 | Kunze |
| 5,376,338 A | 12/1994 | Zlotnik |
| 5,402,517 A | 3/1995 | Gillett et al. |
| 5,497,942 A | 3/1996 | Zingle et al. |
| 5,547,616 A | 8/1996 | Dancs et al. |
| 5,591,395 A | 1/1997 | Schroeder et al. |
| 5,647,053 A | 7/1997 | Schroeder et al. |
| 5,651,942 A | 7/1997 | Christensen |
| 5,662,835 A | 9/1997 | Collingwood |
| D386,974 S | 12/1997 | Wefler |
| D393,063 S | 3/1998 | Wefler |
| 5,891,400 A | 4/1999 | Ansari et al. |
| 5,909,845 A | 6/1999 | Greatbatch et al. |
| 5,919,423 A | 7/1999 | Requejo et al. |
| 5,970,643 A | 10/1999 | Gawel, Jr. |
| 5,980,064 A | 11/1999 | Metroyanis |
| 6,017,139 A | 1/2000 | Lederer |
| 6,071,937 A | 6/2000 | Bretschneider et al. |
| 6,104,867 A | 8/2000 | Stathakis et al. |
| 6,106,786 A | 8/2000 | Akahoshi |
| 6,143,313 A | 11/2000 | Ito et al. |
| 6,196,706 B1 | 3/2001 | Cutts |
| 6,241,161 B1 | 6/2001 | Corbett |
| 6,354,710 B1 | 3/2002 | Nacouzi |
| 6,361,752 B1 | 3/2002 | Demarest et al. |
| 6,371,450 B1 | 4/2002 | Davis et al. |
| 6,391,329 B1 | 5/2002 | Ito et al. |
| 6,416,242 B1 | 7/2002 | Kaufmann |
| 6,446,583 B2 | 9/2002 | Vieira |
| 6,454,425 B1 | 9/2002 | Lin |
| 6,466,739 B2 | 10/2002 | Ambrosi et al. |
| 6,484,438 B2 | 11/2002 | Matsunaga et al. |
| 6,555,068 B2 | 4/2003 | Smith |
| 6,567,613 B2 | 5/2003 | Rymer |
| 6,580,875 B2 | 6/2003 | Rymer |
| 6,616,308 B2 | 9/2003 | Jensen et al. |
| 6,619,560 B1 | 9/2003 | Chun |
| 6,661,967 B2 | 12/2003 | Levine et al. |
| 6,697,571 B2 | 2/2004 | Triplett et al. |
| 6,715,723 B2 | 4/2004 | Zhu |
| 6,766,817 B2 | 7/2004 | da Silva |
| 6,862,403 B2 | 3/2005 | Pedrotti et al. |
| 6,871,794 B2 | 3/2005 | McEwen |
| 6,889,003 B2 | 5/2005 | Triplett et al. |
| 6,899,280 B2 | 5/2005 | Kotary et al. |
| 6,920,282 B2 | 7/2005 | He et al. |
| 6,923,383 B1 | 8/2005 | Joshi et al. |
| 6,931,202 B2 | 8/2005 | Pedrotti et al. |
| 6,938,883 B2 | 9/2005 | Adams et al. |
| 6,966,665 B2 | 11/2005 | Limburg et al. |
| 7,018,644 B2 | 3/2006 | Lang |
| 7,175,815 B2 | 2/2007 | Yamasaki et al. |
| 7,201,916 B2 | 4/2007 | Schiavo et al. |
| 2002/0080601 A1 | 6/2002 | Meltzer |
| 2002/0093834 A1 | 7/2002 | Yu et al. |
| 2002/0136542 A1 | 9/2002 | He et al. |
| 2002/0136886 A1 | 9/2002 | He et al. |
| 2003/0005620 A1 | 1/2003 | Ananth et al. |
| 2003/0007887 A1 | 1/2003 | Roumpos et al. |
| 2003/0053305 A1 | 3/2003 | Lin |
| 2003/0146292 A1 | 8/2003 | Schramm et al. |
| 2004/0065749 A1 | 4/2004 | Kotary et al. |
| 2004/0074982 A1 | 4/2004 | Kotary et al. |
| 2004/0141315 A1 | 7/2004 | Sherburne |
| 2004/0182949 A1 | 9/2004 | Duston et al. |
| 2004/0184969 A1 | 9/2004 | Kotary et al. |
| 2004/0246711 A1 | 12/2004 | Brenchley et al. |
| 2004/0257798 A1 | 12/2004 | Hart |
| 2004/0262419 A1 | 12/2004 | Kotary et al. |
| 2004/0262420 A1 | 12/2004 | Hansen et al. |
| 2004/0265189 A1 | 12/2004 | Schwarz |
| 2004/0265196 A1 | 12/2004 | Varanasi et al. |
| 2005/0053528 A1 | 3/2005 | Rymer |

FOREIGN PATENT DOCUMENTS

| | | |
|---|---|---|
| DE | 299 07 125 U1 | 7/1999 |
| DM | 05 4926 | 9/2000 |

| | | | |
|---|---|---|---|
| EP | 0 882 459 A1 | 12/1998 |
| EP | 1 031 446 A1 | 8/2000 |
| EP | 1 270 021 A1 | 1/2003 |
| EP | 1 283 062 | 2/2003 |
| EP | 1 392 368 | 10/2003 |
| GB | 2285579 A | 7/1995 |
| WO | WO 95/10352 | 4/1995 |
| WO | WO 98/16262 A1 | 4/1998 |
| WO | WO 01/02025 A1 | 1/2001 |
| WO | WO 01/23008 A1 | 4/2001 |
| WO | WO 02/30220 | 4/2002 |
| WO | WO 02/31413 A2 | 4/2002 |
| WO | WO 02/31413 A3 | 4/2002 |
| WO | WO 03/013618 A1 | 2/2003 |
| WO | WO03/086487 A1 | 10/2003 |
| WO | WO 2004/030708 A1 | 4/2004 |

OTHER PUBLICATIONS

International Search Report and Written Opinion, Aug. 16, 2004, Appl. No. PCT/US04/008437.

International Search Report and Written Opinion dated Oct. 26, 2004, Appl. No. PCT/US2004/020237.

"INGLOW™ Candle Company" www.inglowcandle.com (2002).

"Luna Candles" http://www.epartyunlimited.com/luna-candles.html (print date 2005).

Now Smell This, Perfume FAQ: Frequently Asked Questions About Perfume, http://nowsmellthis.blogharbor.com/blog/_WebPages/Perfume_FAQ.html, 2 pages, Print Date Jan. 5, 2007.

Search Report in European Application No. 06024465.4-2113 dated Aug. 21, 2007.

Office Action in European Application No. 04 777 005.2-2113 dated Sep. 15, 2008.

"Axisymmetric Drop Shape Analysis as a Film Balance: Rate Dependent of the Collapse Pressure and Molecular Area at Close Packing of 1-Octadecanol Monolayers," D.Y. Kwok, American Chemical Society, 1996.

Schwarz U.S. Appl. No. 11/341,046, filed Jan. 25, 2006.

Lakatos et al. U.S. Appl. No. 11/341,166, filed Jan. 27, 2006.

VOLATILE LIQUIDS HAVING PREDETERMINED EVAPORATION PROFILES

CROSS REFERENCE TO RELATED APPLICATIONS

This application is a continuation of U.S. patent application Ser. No. 10/608,357 filed Jun. 27, 2003.

BACKGROUND OF THE INVENTION

Field of the Invention

This invention relates generally volatile liquids, and more particularly to volatile liquids having predetermined evaporation rates.

SUMMARY OF THE INVENTION

In one embodiment, a method of selecting a volatile liquid comprises selecting the volatile liquid based on an evaporation rate between about $5 \times 10^{-9}$ and about $10 \times 10^{-8}$ meters per second measured with about 30% of the volatile liquid remaining at room temperature, as measured and calculated by drop shape analysis and providing a wick, wherein about 90% of the volatile liquid evaporates through the wick within a predefined time period under ambient conditions at ambient room temperature when the wick is exposed to the surrounding environment.

In another embodiment, a method of volatizing a liquid comprises the steps of providing a housing and a fan mounted to the housing to generate an air stream, providing a selected volume of a volatile liquid carried within an enclosed reservoir, selecting the volatile liquid based on a predetermined evaporation rate measured with about 30% of the volatile liquid remaining at room temperature, as measured and calculated by drop shape analysis, providing a wick extending between the volatile liquid and the air stream, wherein about 90% of the volatile liquid evaporates through the wick within a predefined time period under ambient conditions at ambient room temperature when the wick is exposed to the surrounding environment, inserting the reservoir into the housing, and operating the fan, wherein the volatile liquid is dispersed out of the housing into the surrounding environment.

In a different embodiment, a method of determining an evaporation time period of a volume of volatile liquid comprises the step of calculating an evaporation profile of the volatile liquid including at least two evaporation rates as measured and calculated by drop shape analysis, a first evaporation rate calculated at a first time and a second evaporation rate calculated at a second time, wherein the evaporation rate at each time is calculated using an equation, wherein the evaporation rate at a time $t = 2(\text{volume at } t_2 - \text{volume at } t_1)/(\text{surface area at } t_2 + \text{surface area at time } t_1)$, where time $t = (t_1 + t_2)/2$.

BRIEF DESCRIPTION OF THE DRAWINGS

Certain embodiments of the presently claimed invention are illustrated by the accompanying figures. It should be understood that the figures are not necessarily to scale and that details which are not necessary for an understanding of the invention or which render other details difficult to perceive may be omitted. It should be understood, of course, that the invention is not necessarily limited to the particular embodiments illustrated herein.

DETAILED DESCRIPTION

Figure 1:
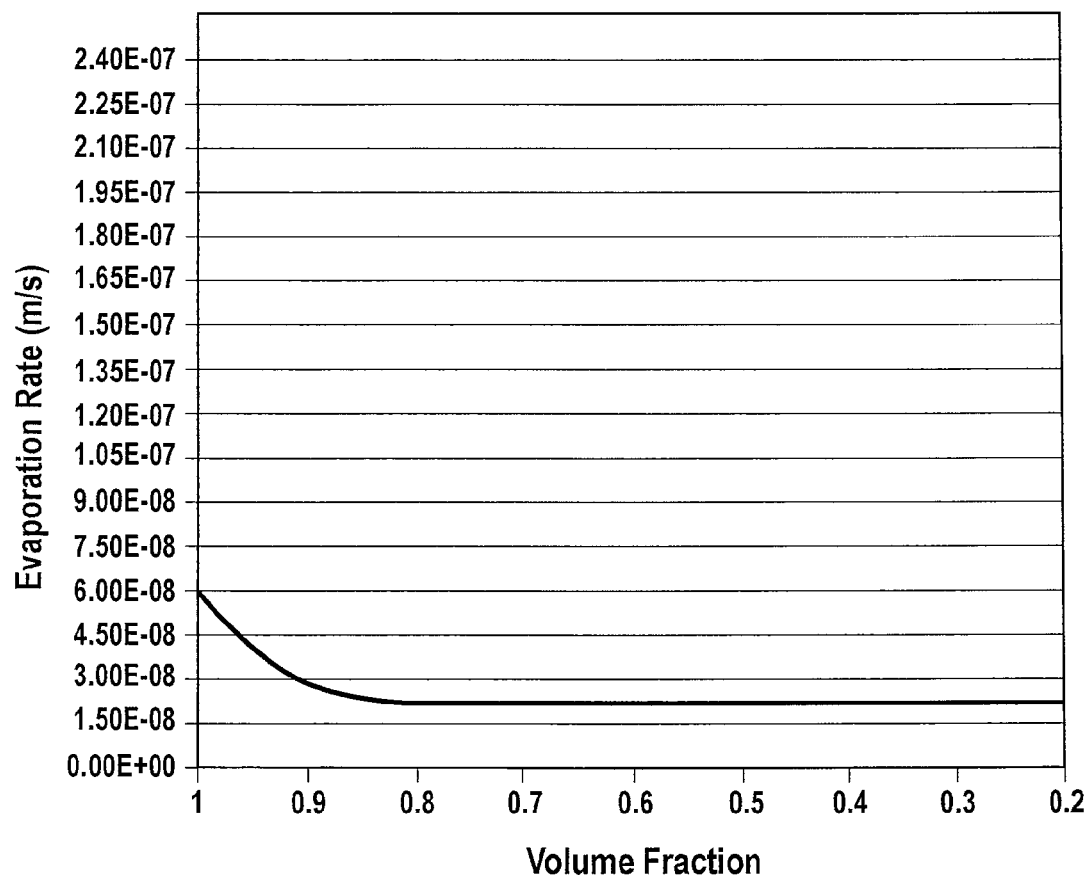
FIG. 1 is a graphical representation of the evaporation rate of a volatile liquid plotted against decreasing volume fractions of volatile liquid remaining.

Dispensers according to the present invention may comprise a volatile liquid and a housing. The dispenser may, however, include additional components, such as a motorized fan and/or a wick, to facilitate release of the volatile liquid into the atmosphere.

The volatile liquid of the present invention has a predetermined evaporation rate. Evaporation rate is defined as the rate at which at least a portion of a liquid changes into a vapor, in meters per second. According to the present invention, the volatile liquid generally has an evaporation rate between about $5.0 \times 10^{-9}$ and about $10.0 \times 10^{-8}$ meters per second, calculated in accordance with the method described below. In select embodiments, the evaporation rate of the volatile liquid is between about $1.0 \times 10^{-8}$ and about $7.0 \times 10^{-8}$.

Examples of volatile liquids for use in the present invention include, but are not limited to dodecane, which exhibits an evaporation rate of about $2.0 \times 10^{-8}$ meters per second and a mixture of dodecane and tetradecane, which exhibits an evaporation rate of about $5.0 \times 10^{-9}$ meters per second, when measured in accordance with the method below. When the mixture is employed, the dodecane and tetradecane are typically present in amounts of 60% to 40% by weight respectively.

In some instances, the volatile liquid is a fragrance. Many known fragrances may be employed. For example, fragrances available from Givaudan S.A. of Great Britain are suitable. Four such fragrances and their evaporation rates, measured at about 30% fluid remaining and room temperature are listed below in the following table:

| Fragrance | Evaporation Rate |
| --- | --- |
| Vanilla | $4 \times 10^{-8}$ |
| Citrus | $2 \times 10^{-8}$ |
| Jasmine and White | $1.5 \times 10^{-8}$ |
| Summer Melon | $1.30 \times 10^{-8}$ |

In other instances, the volatile liquid may be a product for insect control. Insecticides kill insects upon contact with the insecticide or upon ingestion of the insecticide by the insect. Since many insecticides work upon physical contact, insects should be attracted to the insecticide. In one embodiment, this attraction is accomplished through combination of a water-based volatile liquid and an oil-based volatile liquid. The water-based volatile liquid attracts the insects, which seek water for survival, while the oil-based volatile liquid carries the insecticidal agent.

Evaporation rates of the volatile liquids of the present invention are measured and calculated through use of a drop tensionmeter and a high speed digital camera. Measurements should be taken under controlled conditions, including room temperature and a relative humidity of approximately 30% to 50%. Because evaporation rates often change over time, for purposes of the present invention, the evaporation rate is measured and calculated at about 30% of the volatile liquid remaining.

To measure evaporation rate, so-called drop shape analysis, described hereinafter, is employed. First, a pendant drop of about 6.0 microliters of volatile liquid is formed from and placed on a flat clean surface. The droplet is then positioned between a light source and a high speed camera. The camera is typically a digital camera capable of capturing time changing images of the drop. Many digital cameras are acceptable, provided they can capture an image once every minute. Examples of such digital cameras include, but are not limited to those offered by Olympus, Canon and Nikon. Alternatively, non-digital images can be captured once every minute and later digitized to achieve the same result.

To carry out the necessary measurements, the digital camera is connected to a computer and the capture rate is adjusted to capture about 1 image per minute. The computer is loaded with a software program that allows the volume and surface area of the droplet to be determined at every instant an image is captured. An adaptation of the software program, known as Axisymmetric Drop Shape Analysis, originally referenced in Rotenberg, Y. et. al., 93 Journal of Colloid Interface Science, at page 169 (1983) may be employed. The droplet is allowed to evaporate until its volume reaches about 1.8 microliters, as measured by the software program. That is, evaporation continues until about 30% of the volatile liquid remains. Although the period of time for evaporation to the 30% level is dependent on the type of volatile liquid, passage of about 6 to 7 hours is typical.

Based on these volume and surface area measurements, it is possible to calculate the evaporation rate of the volatile liquid at specific points in time according to the following formula:

Evaporation rate at time '$t$'=2(volume at $t_2$−volume at $t_1$)/(surface area at $t_2$ surface area at time $t_1$), where time '$t$'=$(t_1+t_2)/2$.

The variable "$t_1$" corresponds to a first time while the variable "$t_2$" corresponds to a second time. For example, to calculate the evaporation rate of a volatile liquid according to the present invention at a time T of 1 minute, $t_1=0$ and $t_2=2$. Since the evaporation rates of many volatile liquids change over time, it is recommended that $t_1$ and $t_2$ do not vary widely. It is therefore suggested that evaporation rates should be calculated at one minute intervals (e.g., $t_1=1$, $t_2=2$; $t_1=2$, $t_2=3$, etc.) as the volatile liquid disappears over time. Minimizing the difference between $t_1$ and $t_2$ helps to decrease the degree of error associated with the process. If, however, the evaporation rate is relatively slow and does not change much over time, relatively larger differences between $t_1$ and $t_2$ may become acceptable.

The evaporation profile of the citrus fragrance referenced above is illustrated graphically by FIG. 1, which plots evaporation rate against diminishing volume fraction. The evaporation rate was measured at 74° F. As shown in FIG. 1, as the volume fraction of fragrance remaining decreases, the evaporation rate also decreases. The reason for this relationship is that the more volatile components of the fragrance cause a relatively high initial evaporation rate, leaving the less volatile components of the fragrance behind. As the composition of the fragrance comprises an increasing percentage of less volatile components, evaporation rate predictably decreases.

Use of a fragrance of this type provides an initial spike in the release rate of the fragrance when a container holding the fragrance is initially attached to the dispensing device of the present invention. Under these circumstances, an initial spike in the release rate of the active ingredient (e.g., fragrance) allows users to quickly ascertain whether the device is working to freshen the air. Once an optimum level of active ingredient is present in the ambient air of the operating area, however, the release rate of the active ingredient decreases to an amount sufficient to maintain that optimum level because, as shown above in FIG. 1, the evaporation rate decreases as the volume fraction of fragrance decreases.

It is also possible to calculate the relative evaporation rate of the volatile liquid, which may serve as a control for variations in ambient conditions, such as temperature, humidity or airflow. The relative evaporation rate is defined as the evaporation rate of the volatile liquid divided by the evaporation rate of dodecane, measured under identical conditions. In most cases, the relative evaporation rate for volatile liquids of the present invention will fall between about 0.50 and 4.0. By calculating and comparing relative evaporation rates across a number of different ambient conditions, the evaporation rates of tested fragrances may be normalized.

Figure 2:
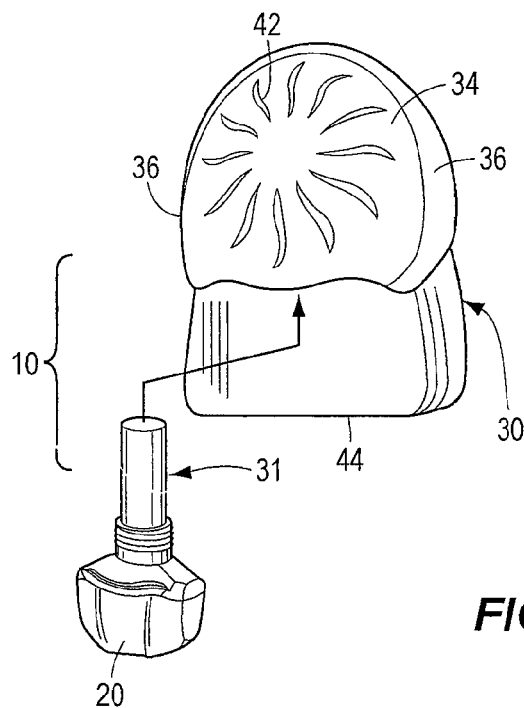
FIG. 2 is a perspective view showing insertion of a wick into a housing of a dispensing device of one embodiment of the present invention.
Figure 3:
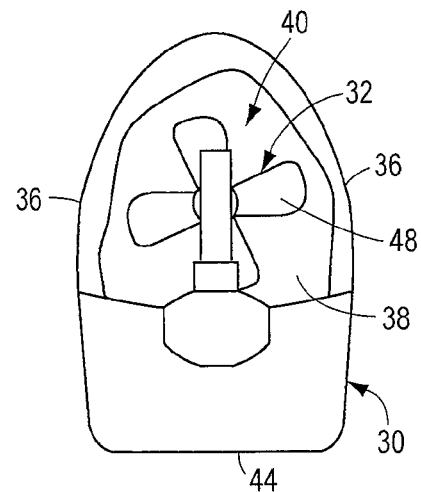
FIG. 3 is a front schematic view of the dispenser of FIG. 2 showing one embodiment of the dispenser housing partially cut away with the wick positioned in the housing.
Figure 4:
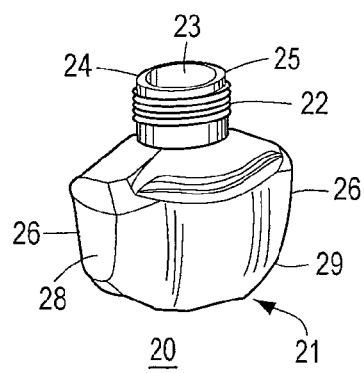
FIG. 4 is a perspective view of the container of FIG. 2.

In other aspects, the present invention involves a dispenser for dispensing volatile liquids having the above-referenced evaporation profiles. Referring now to FIGS. 2-4, volatile liquid dispenser 10 is designed to disseminate a volatile liquid, such as a fragrance, into a room. According to one embodiment, dispenser 10 includes a housing 30, a container 20 for holding the volatile liquid, a motorized fan 32 mounted in housing 30 for generating an air stream, and a wick 31 coupled to container 20.

Figure 5:
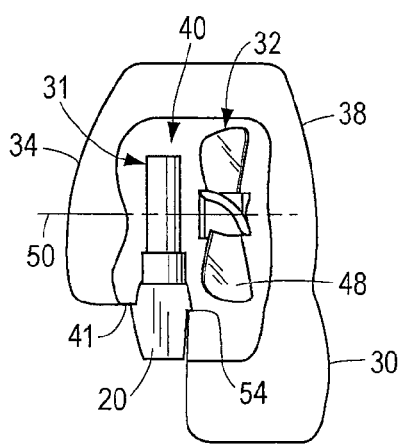
FIG. 5 is a side view showing one embodiment of the dispenser housing partially cut away with the wick positioned in the housing as shown in FIG. 3.

Housing 30, as shown in FIGS. 2, 3 and 5 may include a front wall 34, a side 36 formed at each lateral end of front wall 34, and a rear wall 38 formed opposite front wall 34. Under this construction, front wall 34, sides 36, and rear wall 38 combine to form an enclosure 40 for housing the motorized fan 32 and for receiving wick 31 into the air stream generated by fan 32. A lower portion of housing 30 may form a base 44 configured to enable dispenser 10 to rest on a flat surface.

Container 20 serves as a reservoir for the volatile liquid. Container 20 may be releasably secured to housing 30. As shown in FIG. 4, according to one embodiment of the present invention, container 20 includes a body 21, a neck 22 extending from the body and defining an opening 23 for receiving the volatile liquid therethrough, a pair of opposing sides 24, on opposite sides of the opening, and a pair of sidewalls 26, 27. Each sidewall intersects each of opposing sides 24, 25 at ends thereof. Straight surfaces 28 and 29 may be formed in one or both of sidewalls 26, 27 to aid a user in grasping the container during extraction of the container from the housing.

Container 20 may be secured to housing 30 in a number of ways. For example, container may be secured through an interference fit, a retention structure (described below) or through use of Velcro or other adhesives. The dimensions of container 20 should be such that container 20 fits with housing 30. A portion of container 20 may reside within housing 30 or the container 20 may be positioned entirely within or outside housing 30.

In certain embodiments, container 20 contains a predetermined volume of volatile liquid. Typically, the volume of the volatile liquid is between about 10.0 ml and about 15.0 ml. Most often, the volume of the volatile liquid is about 12.0 milliliters. When the volume of a volatile liquid falls within this range, it is possible to predict the life of the volatile liquid within the container 20 after the container 20 is secured to housing 30, based on the evaporation rates, measured and calculated above. For example, in the absence of a forced air flow, about 90% of a volatile liquid having an evaporation rate of about $8 \times 10^{-8}$ is capable of evaporating within one month in the container of the present invention, while about 90% of a volatile liquid having a second slower evaporation rate of about $2 \times 10^{-8}$ is capable of evaporating in two months.

Figure 6:
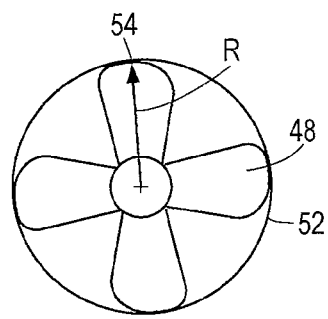
FIG. 6 is a front view of one embodiment of a fan blade assembly mounted in the dispenser housing as shown in FIG. 3.

Housing 30 may also include fan 32 for generating a forced air flow. Fan 32 may be powered by a D battery (not shown) positioned in base 44 of housing 30. Access to the battery may be provided by a hinged or removable access plate formed in base 44. Referring now to FIGS. 3, 5 and 6, fan 32 may include a plurality of fan blades 48 that rotate about a fan axis of rotation 50 during operation of the fan. During rotation, fan blades 48 trace out a circumferential path 52. As shown in FIG. 5, fan blades 48 each have a dimension R extending from axis of rotation 50 to an edge 54 of the respective fan blade 48 farthest from axis of rotation 50. In one embodiment, R is between about 2 cm and about 3 cm.

The operating parameters of fan 32 may vary. In some embodiments, the fan throughput is about 0.4 cubic feet per minute to about 0.45 cubic feet per minute. In other embodiments, the fan exhibits an on/off cycle of about 5 minutes to 15 minutes or a ratio of 1:3. That is, fan may be configured such that it is intermittent. In still other embodiments, the presence of a fan is unnecessary or the fan is simply not turned on.

When dispenser 10 does not include fan 32 or when fan 32 is not turned on, the volatile liquid in container 20 exhibits an evaporation rate of between about $5.0 \times 10^{-9}$ and about $10.0 \times 10^{-8}$, measured at 30% fluid remaining. Of course, incorporation and use of fan 32 with dispenser 10 increases the evaporation rate of the volatile liquid. It should be noted, however, that evaporation rates for the volatile liquids disclosed herein are measured and calculated in the absence of a forced air flow.

Housing 30 may include additional structure for facilitating operation of fan 32. One or more air inlet ports (not shown) may be formed in rear wall 38 for providing intake air for fan 32. Also, as shown in FIG. 2, one or more air outflow ports 42 may be provided in front wall 34 to provide a path for outflow of the air stream from enclosure 40. A switch or button (not shown) may be provided on an exterior surface of housing 30 to enable activation and deactivation of the fan motor.

Container 20 or housing 30 may optionally include wick 31. Wick 31 may be positioned and secured in housing 30, so as to reside in the air stream generated by fan 32. Wick 31 may be secured in the desired position by coupling wick 31 to dispenser housing 30 using any one of numerous methods. For example, in one embodiment, shown in FIGS. 2 and 5, wick may be secured in container 20 holding the volatile liquid to be dispensed. A portion of wick 31 may be in communication with the volatile liquid in container 20. Another portion of wick 31 may extend outside container 20 for immersion into the air stream.

Referring to FIG. 5, dispenser housing 30 has opposing sidewalls 41 and 71. Each of opposing sidewalls 41 and 71 has a corresponding edge portion 58 and 60, respectively. Edge portions 58 and 60 define an opening adapted to receive wick 31 and a portion of container 20 into enclosure 40. A retention structure is formed along one or more of opposing sides of container 20 to help position and releasably secure container 20 between opposing sidewalls 41 and 71 of housing 30. The retention structure may be formed integral with container 20.

Wick 31 can be made of a variety of materials. Polymeric wicks, for example, have been found to be effective for these purposes. In particular, wicks composed of ultra high molecular weight, high density polyethylene (HDPE) have been found to be suitable. Such wicks are generally comprised of blends of HDPE in particle form, and the blends are developed to meet the target pore characteristics of the wick 31.

In one embodiment, the solubility parameter of the polymer is significantly different from that of any of the components contained in the liquid. This prevents the wick 31 from swelling, or other changes, which can lead to a change in the pore size and porosity. If the pore size or porosity of the wick 31 is altered, the release rate of the volatile liquid into the ambient air would also be affected.

In one embodiment, wick 31 comprises a first section made of a material that has a predetermined pore size and a second section made of a material that has a pore size that is greater than that of the material of the first section. The pore size of the first section and second section may vary depending upon the composition of the volatile liquid to be dispersed into the air. In certain embodiments, the ratio of the large pore size to that of the small pore size may be above about two, above about five, and even about above ten. For example, if the large pore size is around ten microns, the small pore size is most preferably below one micron.

Of course, wick 31 can take many different shapes and forms. For example, a wick that has a large pore section of cylindrical shape situated at the top of and around an inner small pore section, also of a cylindrical shape, may be employed. It is advantageous to dispose the small pore section in the area where the liquid is most likely to spill, to minimize the likelihood of liquid spilling or leaking through the wick 31. In particular, the small pore size section may extend into the container 20 and is in contact with the volatile liquid. In this manner, the smaller pores of the inner portion of the wick 31 prevent leakage, while the larger pores of the outer portion provide a maximum release rate of the volatile liquid off the surface of the wick 31 that is exposed to the ambient air.

The mean pore size of the wick 31 can be determined by any standard test for determining porosity and pore size distribution. Mercury porosimetry is a method that gives information on porosity and pore size distribution for rigid wicks. It is based on the measurement of differential increments in the amount of mercury intruded into the wick as a function of increasing applied pressure.

Variations, modifications and other implementations of what is described herein will occur to those of ordinary skill in the art without departing from the spirit and scope of the invention. Accordingly, the invention is in no way limited by the preceding illustrative description.

INDUSTRIAL APPLICABILITY

The present invention has applicability to dispensers for volatile liquids. This includes air fresheners for dispensing fragrances into both large and small areas. I claim:

We claim:

1. A method of selecting a volatile liquid, comprising:
   selecting the volatile liquid based on an evaporation rate between about $5 \times 10^{-9}$ and about $10 \times 10^{-8}$ meters per second measured with about 30% of the volatile liquid remaining at room temperature, as measured and calculated by drop shape analysis; and
   providing a wick, wherein about 90% of the volatile liquid evaporates through the wick within a predefined time period between about one and about two months under ambient conditions at ambient room temperature when the wick is exposed to the surrounding environment.

2. The method of claim 1, further comprising the step of providing between about 12 ml to about 15 ml of the selected volatile liquid based on the evaporation rate.

3. A method of volatizing a liquid, comprising:
providing a housing and a fan mounted to the housing to generate an air stream;
providing a selected volume of a volatile liquid carried within an enclosed reservoir,
selecting the volatile liquid based on a predetermined evaporation rate between about $5 \times 10^{-9}$ and about $10 \times 10^{-8}$ meters per second measured with about 30% of the volatile liquid remaining at room temperature, as measured and calculated by drop shape analysis;
providing a wick extending between the volatile liquid and the air stream, wherein about 90% of the volatile liquid evaporates through the wick within a predefined time period between about one month to about two months under ambient conditions at ambient room temperature when the wick is exposed to the surrounding environment;
inserting the reservoir into the housing; and
operating the fan, wherein the volatile liquid is dispersed out of the housing into the surrounding environment.

4. The method of claim 3, wherein the selected volume is between about 10 ml and about 15 ml.

5. The method of claim 3, wherein the evaporation rate is between about $1 \times 10^{-8}$ and about $7 \times 10^{-8}$ meters per second measured with about 30% of the volatile liquid remaining at room temperature, as measured and calculated by drop shape analysis.

6. The method of claim 5, wherein about 90% of the volatile liquid evaporates in about 2 months under ambient conditions.

7. The method of claim 3, wherein the volatile liquid has a relative evaporation rate of between about 0.5 and about 4.

8. The method of claim 3, wherein the fan exhibits a throughput of about 0.4 cubic feet per minute to about 0.45 cubic feet per minute.

9. The method of claim 8, wherein the air stream is intermittently on and off in a ratio of about 1 minute to 3 minutes.

10. The method of claim 3, wherein the volatile liquid comprises a fragrance.

11. The method of claim 3, wherein the volatile liquid is contained within a container that is adapted to be releasably secured to the housing.

12. A method of determining an evaporation time period of a volume of volatile liquid, comprising the step of:
calculating an evaporation profile of the volatile liquid including at least two evaporation rates as measured and calculated by drop shape analysis, a first evaporation rate is between about $1 \times 10^{-8}$ and about $7 \times 10^{-8}$ meters per second measured with about 30% of the volatile liquid remaining at room temperature, as measured and calculated by drop shape analysis, and is calculated at a first time and a second evaporation rate calculated at a second time, wherein the evaporation rate at each time is calculated using an equation, wherein the evaporation rate at a time $t = 2(\text{volume at } t_2 - \text{volume at } t_1)/(\text{surface area at } t_2 + \text{surface area at time } t_1)$, where time $t = (t_1 + t_2)/2$.

13. The method of claim 12, wherein the first time is calculated using $t_1 = 0$ minutes and $t_2 = 2$ minutes.

14. The method of claim 13, wherein the second time is calculated using $t_1 = 1$ minute and $t_2 = 3$ minutes.

15. The method of claim 12, wherein the first evaporation rate is measured at about 80% of the volatile liquid remaining at room temperature, as measured and calculated by drop shape analysis, wherein the second evaporation rate is measured at about 30% of the volatile liquid remaining at room temperature, as measured and calculated by drop shape analysis, and wherein the first evaporation rate is approximately equal to the second evaporation rate.

16. The method of claim 12, wherein the evaporation rate of the volatile liquid remains at a substantially constant level after about 0.8 volume fraction of the liquid is remaining.

* * * * *